United States Patent [19]

Yamauchi et al.

[11] 4,230,690
[45] Oct. 28, 1980

[54] HIGH-VISCOSITY EYE LOTIONS

[75] Inventors: Aizo Yamauchi, Atsugi; Yasuo Matsuzawa, Machida; Sadayoshi Kamiya, Nagoya; Keisuke Nishioka, Yao; Yoshiaki Hara, Kashiwara; Shogo Matsushima, Nara, all of Japan

[73] Assignees: Director-General of the Agency of Industrial Science and Technology, Tokyo; Nihon, Tenganyaku Kenkyusho K.K., Aichi, both of Japan

[21] Appl. No.: 33,523

[22] Filed: Apr. 26, 1979

[30] Foreign Application Priority Data

Apr. 30, 1978 [JP] Japan ................................. 53-51098

[51] Int. Cl.$^3$ ............................................. A61K 31/74
[52] U.S. Cl. ..................................................... 424/78
[58] Field of Search ........................................... 424/78

[56] References Cited

U.S. PATENT DOCUMENTS

| 3,639,576 | 2/1972 | Kaspar et al. | 424/78 |
| 3,863,633 | 2/1975 | Ryde et al. | 424/78 |
| 3,868,445 | 2/1975 | Ryde et al. | 424/78 |
| 4,003,991 | 1/1977 | Krohn et al. | 424/78 |

OTHER PUBLICATIONS

Symposium on Ocular Therapy 9, 1-16 (1977), Maichuk.

Primary Examiner—Douglas W. Robinson
Attorney, Agent, or Firm—William J. Daniel

[57] ABSTRACT

The invention presents a high-viscosity eye lotion with which lasting curative effects can be obtained with no feeling of foreign bodies to the eye as in the conventional eye salves used in treating eyes.

The high-viscosity eye lotion of the invention comprises a swollen hydrated gel of a crosslinked polyvinyl alcohol and an eye-disease curative active ingredient contained therein. It is prepared by irradiating an aqueous solution of a polyvinyl alcohol with an ionizing radiation to such an extent that the polyvinyl alcohol is crosslinked to give a hydrated gel with an equilibrium swelling ratio in the range from 70 to 100 by weight and then dipping the hydrated gel in an aqueous solution of the eye-disease curative active agent.

6 Claims, 5 Drawing Figures

HIGH-VISCOSITY EYE LOTIONS

BACKGROUND OF THE INVENTION

The present invention relates to a high-viscosity eye lotion capable of exhibiting extended effectiveness over a long time when dropped in the eye. More particularly, the invention relates to a high-viscosity eye lotion prepared with a specific hydrated polymer gel as the base and a method for preparing the same.

Hitherto, when extended effectiveness of an eye lotion is desired or a sustained-release eye lotion is to be used, it has been usual in the prior art therapeutics to prescribe an eye salve prepared with a white vaseline as the base or carrier medium. These vaseline-based eye salves are defective because of poor releasability of the active ingredients as well as poor stability of the curative effect over a long time after application to the eye. An improved eye salve has been proposed which is prepared with certain synthetic polymeric substances as the base (see, for example, "Yakuzai-gaku" (Pharmaceutics), vol. 19, No. 4, p. 17 (1959)). This kind of base material has somewhat improved releasability of the active ingredients in comparison with vaselines but is deficient in wettability of the cornea. Furthermore, such a synthetic base material causes a feeling of foreign bodies to the patient when applied to the eye. Thus, no satisfactory sustained-release eye-lotion is available hitherto despite a definite need therefor in eye therapeutics.

SUMMARY OF THE INVENTION

The present invention is the result of extensive investigations by the inventors undertaken with the object of solving the above described problems in the prior art sustained-release eye lotions or eye salves and to develop an eye lotion with extended effectiveness over a long time following introduction giving a stable curative action without any feeling of foreign bodies to the eye.

According to the invention, a high-viscosity eye lotion invention comprises a crosslinked hydrated gel of polyvinyl alcohol (hereinafter abbreviated as PVA) as the base or carrier medium having an equilibrium swelling ratio in water in the range from 70 to 100 by weight at room temperature and an eye-disease curative active ingredient.

Further the invention includes a method for preparing the above high-viscosity eye lotion which comprises irradiating an aqueous solution of a PVA with an ionizing radiation to such an extent that the PVA in the aqueous solution is crosslinked to have an equilibrium swelling ratio in water in the range from 70 to 100 by weight at room temperature and impregnating the thus obtained hydrated gel with an ophthalmically active ingredient to a desired therapeutically effective concentration.

DETAILED DESCRIPTION OF THE PREFERRED EMBODIMENTS

Figure 1:
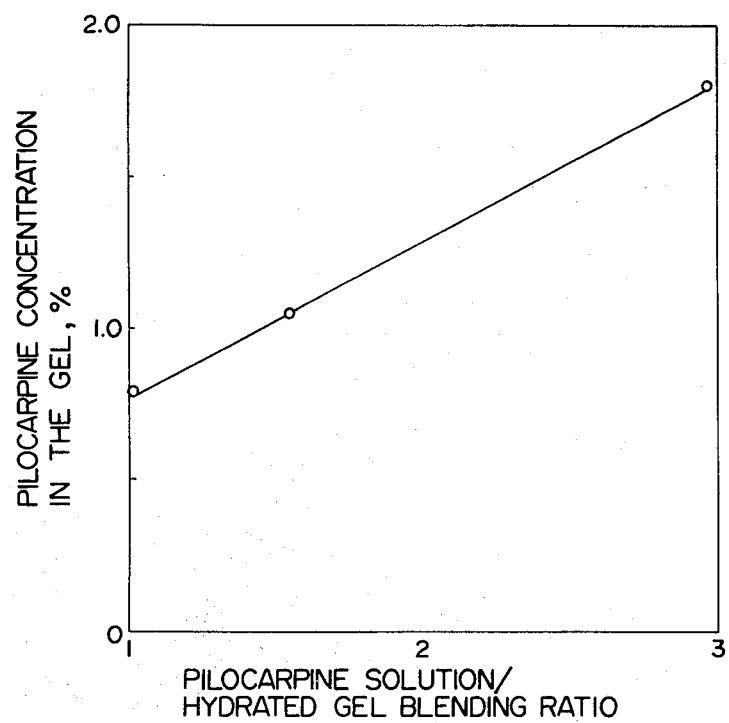
FIG. 1 is a graphic showing of the relationship between the blending ratio by weight of the 2%-pilocarpine solution to the hydrated PVA gel and the concentration of the pilocarpine in the pilocarpine-impregnated hydrated gel.

The base material of the inventive high-viscosity eye lotion is a hydrated gel of a crosslinked PVA and the hydrated gel is obtained by irradiating an aqueous solution of a PVA with ionizing radiation to crosslink the PVA.

The PVA as the starting material may be a fully saponified PVA or a partially saponified PVA and the average degree of polymerization of the PVA is preferably in the range from 500 to 2500.

The method for crosslinking the PVA is not limited to irradiation with ionizing radiation but this is the most convenient way to achieve radiation crosslinking and the kind of the ionizing radiation is also not limited although gamma rays from cobalt-60 radioisotope is recommended for reasons of handiness and effectiveness. The irradiation with gamma rays is carried out with an aqueous solution of the PVA in a concentration, preferably, from 1 to 20% by weight and the irradiation is continued in an inert atmosphere such as nitrogen until the PVA has been crosslinked to have an equilibrium swelling ratio in water, as defined by the weight ratio of the hydrated gel to the dried gel, equal to 70 to 100 by weight at room temperature. The total dosage of the gamma rays depends on several factors but ranges usually from 0.5 to 1.0 Mrads. When the swelling ratio of the PVA is smaller than 70 by weight, resultant hydrated gels have poor flowability so that the eye lotion prepared therewith cannot function satisfactorily while the viscosity of a hydrated PVA gel with a swelling ratio larger than 100 by weight is too low so that the duration of effectiveness of an eye lotion prepared therewith is decreased.

The hydrated PVA gel obtained as above is a viscous, clear fluid having physical properties close to human tears and has good retention and releasability of medicines impregnated therein as well as good wettability on the cornea so that it is retained substainedly in the saccus conjunctivae. A further advantage of hydrated PVA gel is the absence of a feeling of foreign bodies by the patient when it is dropped to the eye.

The hydrated PVA gel may be impregnated with various kinds of eye-disease curative, i.e. ophthalmically active, ingredients but suitable among them are pupil-contracting agents such as pilocarpine and the like, mydriatics such as tropicamide and the like, bactericides such as iodine and the like, antibiotics such as chloramphenicol and the like, antiphlogisticas such as dexamethasone and the like, and eye-washing agents such as boric acid as well as other medically active ingredients conventionally used as a curative agent of eye diseases.

The impregnation of the hydrated PVA gel with the above given active ingredients is carried out by dipping the hydrated gel in an aqueous solution containing a sufficient amount of the active ingredient in a therapeutically effective concentration of, for example, 0.05 to 5% by weight for a few hours to several tens of hours at room temperature whereby the active ingredient migrates to the hydrated PVA gel from the solution to give a high-viscosity eye lotion of the present invention.

The concentration of the therapeutically active ingredient in the hydrated PVA gel is not limited insofar as a therapeutical effectiveness is obtained although the upper limit is given at about 5% since the hydrated gel with a higher concentration of the active ingredient is excessively hypertonic. On the contrary, no lower limit exists because any smallest concentration, say, of 0.001% or smaller can be sufficiently effective depending on the activity of the ingredient although most of the conventional eye-disease curative ingredients are effective with a concentration of 0.05 to 5%.

Different from conventional eye lotions which readily flow out of the eyes after dropping, the high-viscosity eye lotion of the present invention can be retained within the eye for 10 hours or longer to release the active ingredient continuously so that the inventive eye lotions can be used very advantageously for therapeutic treatment of various kinds of eye diseases. Furthermore, because of the similarity of the physical properties of the hydrated PVA gel to human tears, the inventive eye lotions bring about no feeling of foreign bodies or irritation to the eye and causes no adverse effects such as hyperemia in the conjunctiva. It is also possible to further improve the wettability on the cornea by the addition of a protein or a mucoid thereto.

Following are examples to illustrate the present invention in further detail.

EXAMPLE 1

(Preparation of a hydrated PVA gel)

Portions of a 7% by weight aqueous solution of a fully saponified PVA with an average degree of polymerization of about 2000 were sealed each in a 5 ml capacity glass ampule after evacuation and filling with nitrogen gas and the ampules were subjected to irradiation with gamma rays from a source of cobalt-60 at a dose rate of 0.1 Mrad/hour for 6 hours at room temperature to give a total dose of 0.6 Mrad.

After the end of the above irradiation time, the ampule was opened and the albumen-like hydrated gel was taken out of the ampule and poured into 100 ml of boiling water where it was kept for about 5 minutes. Thereafter, the mixture containing the fully swollen PVA gel was poured over a filter cloth of polyvinylidene chloride and the gel material on the filter cloth was recovered to be used in the subsequent preparation of the inventive eye lotions.

The equilibrium swelling ratio of the hydrated PVA gel, i.e. the weight ratio of the hydrated gel to the dry weight of the crosslinked PVA contained therein, was about 80 at room temperature giving a water content of about 99% in the hydrated gel.

EXAMPLE 2

The hydrated PVA gel obtained in Example 1 and a 2% aqueous solution of commercial grade pilocarpine were blended in varied proportions and the blend was kept standing for 24 hours at room temperature to establish equilibrium to give a high-viscosity eye lotion. The concentration of the pilocarpine in the finished eye lotion was dependent on the blending ratio of the hydrated PVA gel and the aqueous pilocarpine solution as shown in FIG. 1 giving the relationship between the blending ratio by weight and the concentration of the pilocarpine in the eye lotion determined by the ultraviolet absorption spectroscopic analysis at a wavelength of 215 nm.

Figure 2:
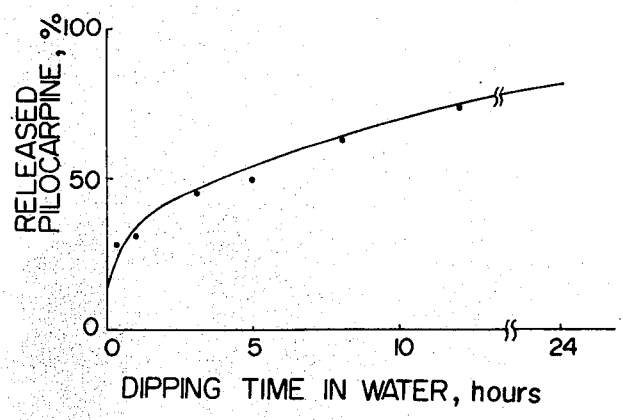
FIG. 2 shows the relationship between the dipping time of the pilocarpine-impregnated hydrated gel in water and the released amount of pilocarpine.

FIG. 2 shows the velocity of release of the pilocarpine in distilled water from the eye lotion prepared in the above manner containing 1.0% by weight of pilocarpine, the time of dipping in hours being indicated on the abscissa and the released amount in % the ordinate.

Figure 3:
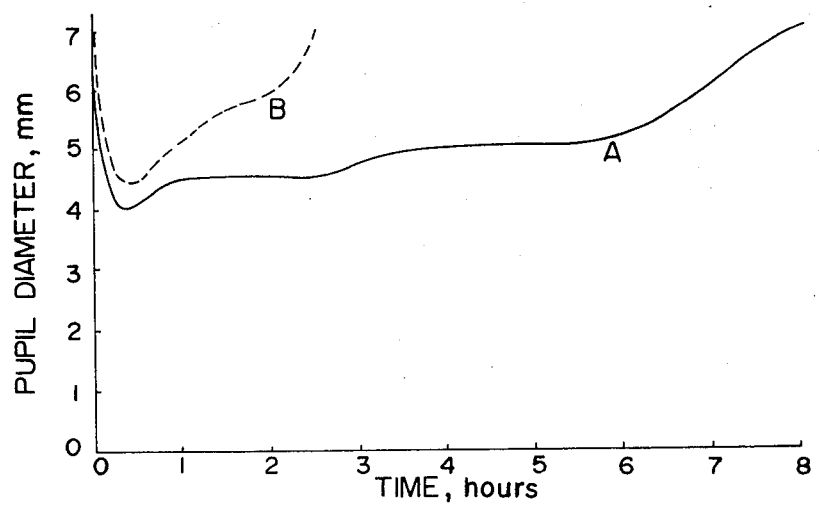
FIG. 3 shows the contraction and recovery of the diameter of pupils of rabbit eyes treated with pilocarpine containing eye lotions wherein curve A represents a lotion according to the present invention while curve B represents a control.

An in vivo test was undertaken for the same eye lotion with rabbits as the test animal. Thus 3 drops each of the inventive high-viscosity eye lotion and a conventional eye lotion of a physiological saline solution containing 1.0% by weight of pilocarpine were dropped to the right and the left eyes, respectively, of rabbits and the diameters of the pupils were measured from time to time until complete recovery to the normal state. The results are shown in FIG. 3.

EXAMPLE 3

A high-viscosity eye lotion containing 0.05% by weight of tropicamide as a mydriatic was prepared in the same manner as in Example 2 above by use of a hydrated PVA gel with an equilibrium swelling ratio of 75 at room temperature obtained by the gamma-ray irradiation of 0.54 Mrad and an in vivo test was undertaken with this high-viscosity eye lotion and a conventional eye lotion of a physiological saline solution containing 0.05% by weight of tropicamide as the control by use of rabbits as the test animal. The test procedure was the same as in Example 2.

With each of the eye lotions tested, the diameter of the pupil was increased from 4.0 mm to 8.0 mm and gradually regained the initial diameter of 4.0 mm taking only 3 hours for the control eye lotion while the diameter of the pupil treated with the inventive eye lotion remained 8.0 mm after 12 hours from dropping and regained the initial diameter of 4.0 mm only after 15 hours from dropping.

Figure 4:
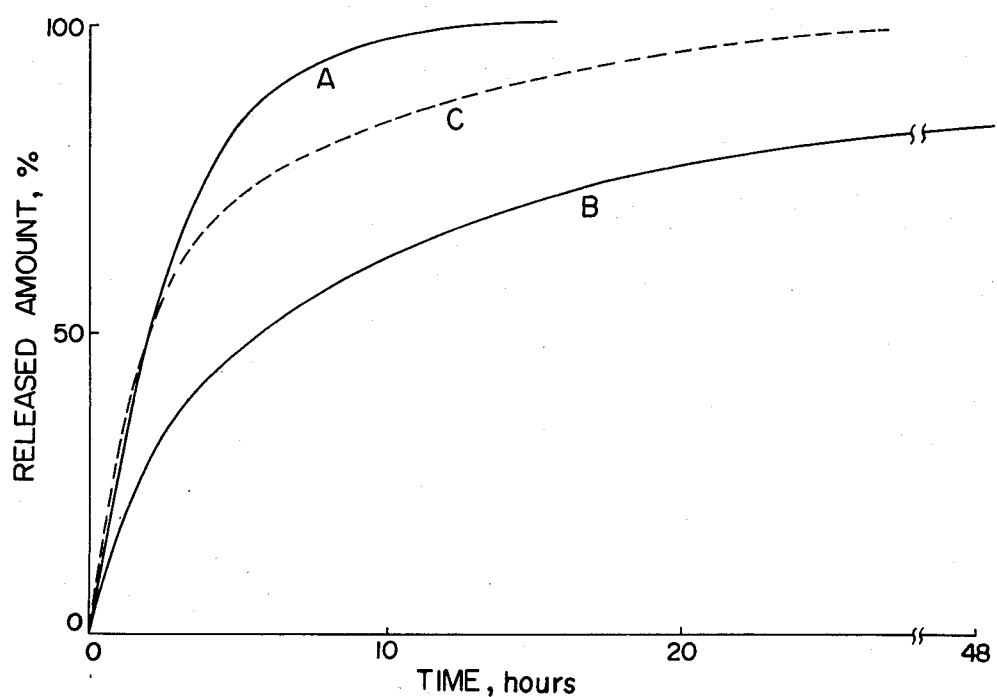
FIG. 4 shows the results of the elution tests with tropicamide-, chloramphenicol- and dexamethasone-impregnated hydrated PVA gels. Curve A: tropicamide; curve B: chloramphenicol; and curve C: dexamethasone.

An in vitro test was undertaken to demonstrate the durability of the effectiveness with the inventive high-viscosity eye lotion. Thus, a high-viscosity eye lotion of hydrated PVA gel containing 0.25% by weight of tropicamide was prepared in the same manner as above and a glass column of 10 mm diameter was filled with 1.0 g of the hydrated gel which was subjected to elution with a physiological saline solution at a flow rate of 12 ml/hour. The concentration of tropicamide in the effluent solution was determined periodically by the ultraviolet absorption spectroscopic analysis at a wavelength of 257 nm. The results are shown in FIG. 4 as curve A, the time of elution in hours appearing along the abscissa and the accumulated amount in % of tropicamide in the effluent solution along the ordinate. As is evident from FIG. 4, the tropicamide contained in the hydrated PVA gel was released almost completely within 12 hours, to be in approximate coincidence with the in vivo test by use thus closely corresponding with the in vivo test results above.

EXAMPLE 4

High-viscosity eye lotions of hydrated PVA gels containing 0.05% by weight of chloramphenicol as an antibiotic or 0.05% by weight of dexamethasone as an antiphlogistic, respectively, in the same manner as in Example 2 by use of a hydrated PVA gel with an equilibrium swelling ratio of 95 at room temperature obtained by the gamma-ray irradiation of 0.66 Mrads.

In vitro tests with glass columns were undertaken in the same manner as in the preceding example to give the results shown in FIG. 4 by the curves B and C giving the relationships between the time of elution in hours and the accumulated amounts in % of the eluted active ingredients. As is evident from the figure, both of the high-viscosity eye lotions exhibited very durable activity and, in particular, the activity of the chloramphenicol-containing eye lotion lasted for 24 hours or longer.

EXAMPLE 5

Figure 5:
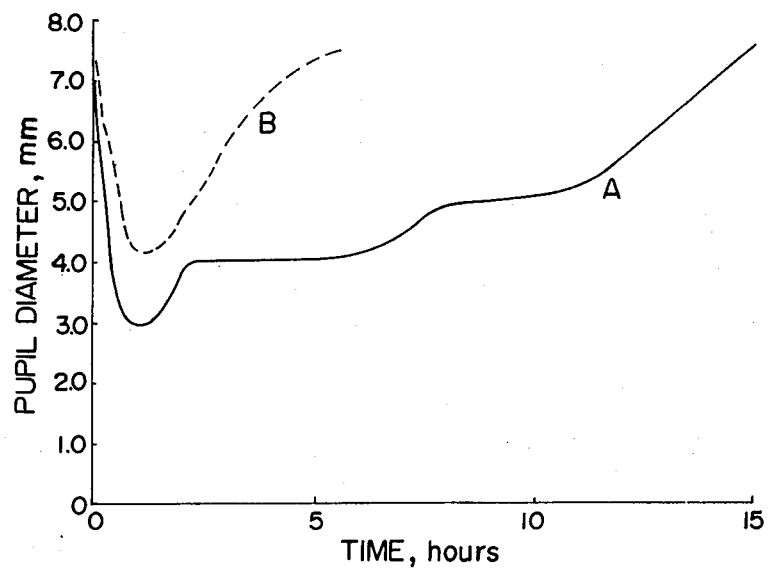
FIG. 5 shows the contraction and recovery of the diameter of pupils of human eyes treated with eye lotions. Curve A: present invention; curve B: control.

Three drops each of the same high-viscosity eye lotion used in the in vivo test with rabbits in Example 2 containing 1.0% by weight of pilocarpine and the same control eye lotion were dropped into normal human eyes and the diameters of the pupils were measured from time to time after dropping to give the results shown in FIG. 5. The difference between both of the eye lotions was very significant in the duration of activity.

COMPARATIVE EXAMPLE

Pilocarpine-impregnated hydrated PVA were prepared in the same manner as in Example 2 by use of hydrated PVA gels prepared in the same manner as in Example 1 except that the equilibrium swelling ratios of the gels were made to be 65 or 150 at room temperature, respectively, by decreasing or increasing the total dose of the gamma-ray irradiation.

The resultant eye lotion with low equilibrium swelling ratio of 65 was too viscous to be dropped into the eye while the viscosity of the eye lotion with high equilibrium swelling ratio of 150 was too low giving poor duration of therapeutic activity when dropped into the eye.

What is claimed is:

1. high-viscosity eye lotion comprising a flowable swollen hydrated gel of a cross-linked polyvinyl alcohol having an equilibrium swelling ratio in the range from 70 to 100 by weight at room temperature as a carrier medium and an ophthalmically active ingredient in a therapeutically effective concentration in said carrier medium.

2. The high-viscosity eye lotion as in claim 1 wherein the eye-disease curative active ingredient is selected from the group consisting of pupil-contracting agents, mydriatics, antiphlogisticas and antibiotics.

3. A method for preparing a high-viscosity eye lotion which comprises subjecting an aqueous solution of a polyvinyl alcohol to irradiation with an ionizing radiation to such an extent that the polyvinyl alcohol is crosslinked to give a hydrated gel with an equlibrium swelling ratio in the range from 70 to 100 by weight at room temperature and impregnating the thus obtained hydrated gel of the crosslinked polyvinyl alcohol with an eye-disease curative active ingredient in a therapeutically effective concentration.

4. The method as claimed in claim 3 wherein the impregnation is carried out by dipping the hydrated gel in an aqueous solution of the eye-disease curative active ingredient.

5. The method as claimed in claim 3 wherein the irradiation is carried out with gamma rays to a total dose of about 0.5 to about 1.0 megarad.

6. The method as claimed in claim 3 wherein the concentration of the aqueous solution of the polyvinyl alcohol is in the range from about 1% to about 20% by weight.

* * * * *